(12) United States Patent
Mathiesen et al.

(10) Patent No.: US 7,919,470 B2
(45) Date of Patent: Apr. 5, 2011

(54) GLYCOPEPTIDE COMPOSITION WITH IMPROVED ANTIBIOTIC ACTIVITY

(75) Inventors: Anita Mathiesen, Stabekk (NO); Torben Koch, Copenhagen_NV (DK); Trine Suhr-Jessen, Gentofte (DK); Joern Thyme, Roskilde (DK); Tiemen Geert Pieter Reijns, Den Haag (NL)

(73) Assignee: Xellia Pharmaceuticals APS (DK)

( * ) Notice: Subject to any disclaimer, the term of this patent is extended or adjusted under 35 U.S.C. 154(b) by 887 days.

(21) Appl. No.: 10/572,160

(22) PCT Filed: Sep. 17, 2004

(86) PCT No.: PCT/DK2004/000632
§ 371 (c)(1),
(2), (4) Date: Jun. 11, 2007

(87) PCT Pub. No.: WO2005/025599
PCT Pub. Date: Mar. 24, 2005

(65) Prior Publication Data
US 2007/0287663 A1 Dec. 13, 2007

(30) Foreign Application Priority Data
Sep. 17, 2003 (EP) .................................... 03021000

(51) Int. Cl.
*A01N 37/18* (2006.01)
*A01N 43/04* (2006.01)
*A61K 38/00* (2006.01)
*A61K 31/70* (2006.01)

(52) U.S. Cl. .............................................. 514/25; 514/2

(58) Field of Classification Search .................. 514/2, 25
See application file for complete search history.

(56) References Cited

U.S. PATENT DOCUMENTS

| 4,239,751 A | 12/1980 | Coronelli et al. |
| 4,994,555 A | 2/1991 | Panzone et al. |

OTHER PUBLICATIONS

Nagarajan, R., Schabel, A.A. (1988) Selective Cleavage of Vancosamine, Glucose, and N-Methyl-Leucine from Vancomycin and Related Antibiotics. Journal of the Chemical Society, Chemical Communications, p. 1306-1307.*
Kaplan, J., Korty, B.D., Axelsen, P.H., Loll, P.J. (2001) The Role of Sugar Residues in Molecular Recognition by Vancomycin. Journal of Medicinal Chemistry, vol. 44, p. 1837-1840.*
Remington: The Science and Practice of Pharmacy, 20th Edition, editor Daniel Limmer, published by the University of the Sciences in Philadelphia (2000) p. 858-863.*
Coronelli, C. et al., "Teicoplanin: Chemical, Physico-chemical and Biological Aspects," Farmaco, Edizione Scientifica, 42(10); pp. 767-786 (1987) XP009025779.
Malabarba, Adriano, et al., "Teicoplanin, Antibiotics from Actinoplanes Teichomyceticus NOV. SP.: VI. Chemical Degradation: Physico-Chemical and Biological Properties of Acid Hydrolysis Products," Journal of Antibiotics Japan, vol. 37(9): pp. 988-999 (1984) XP009025805.
Wanner, Jutta, et al., "A New and Improved Method for Deglycosidation of Glycopeptide Antibiotics Exemplified with Vancomycin, Ristocetin, and Ramoplanin," Bioorganic and Medicinal Chemistry Letters, 13 (6); pp. 1169-1173; XP002314492; (2003).
Yao, Raymond C., et al.; "Glycopeptides, Classification, Occurrence, and Discovery in Glycopeptide Antibiotics,"; in Glycopeptide Antibiotics; ed. Nagarajan, R., Marcel Dekker, Inc., Chapter 1, pp. 1-27 (1994).
Goldstein, B. et al, "Teicoplanin in Glycopeptide Antibiotics,"; in Glycopeptide Antibiotics; ed. Nagarajan, R., Marcel Dekker, Inc. N.Y., N.Y. Chapter 8, pp. 273-307; (1994).
Parenti, F., et al.; "Teicoplanin Chemistry and Microbiology"; Journal of Chemotherapy, vol. 12, Supplement n. 5; pp. 5-14 (2000).
Janknegt, R.; "Teicoplanin in Perspective," Pharmaceutisch Weekblad Scientific Edition, 13(4); pp. 153-160; (1991).
Reynolds, P. E., "Structure, Biochemistry and Mechanism of Action of Glycopeptide Antibiotics"; Eur. J. Clin. Microbiol. Infect. Dis.; 8(11); pp. 943-950; (1989).
March, Jerry; "Aliphatic Nucleophilic Substitution"; in Advanced Organic Chemistry, Reactions, Mechanisms, and Structure, 4th Edition; John Wiley & Sons, New York, ISBN 0-471-60180-2; pp. 388-396 (1992).
Tanaka, K., et al.; "Structure-Activity Relationships in Tetronic Acids and Their Copper (II) Complexes"; Chem. Pharm. Bull., 27(8); pp. 1901-1906 (1979).
Matsuo, K., et al.; "Structure-Activity Relationships in Tetramic Acids and Their Copper (II) Complexes"; Chem. Parm. Bull.; 28(8); pp. 2494-2502; (1980).
Rylander, Paul N.; "Hydrogenation of Olefins"; Academic Press Inc.; San Diego; Chpt. 2; pp. 29-53; ISBN 0-12-605366-9; (1985).
House, Herbert, O.; "Halogenation: Alkyl halides from Olefins or Alcohols"; in Modern Synthetic Reactions; Second Edition, W.A. Benjymin, Inc., New York, pp. 446-459 (1972).
Schroder, Martin; "Osmium Tetraoxide Cis Hydroxylation of Unsaturated Substrates"; Chem. Rev.; 80; pp. 187-213; (1980).
March, Jerry; "Addition to Carbon-Carbon Multiple Bonds: Reactions"; in Advanced Organic Chemistry, 4th Edition; John Wiley & Sons; pp. 826-829; ISBN 0-471-60180-2; (1992).

* cited by examiner

*Primary Examiner* — Shaojia Anna Jiang
*Assistant Examiner* — Scarlett Goon
(74) *Attorney, Agent, or Firm* — Cantor Colburn LLP

(57) ABSTRACT

A glycopeptide composition with improved antibiotic activity is disclosed, along with a method of preparing such a composition and a pharmaceutical composition made therefrom.

6 Claims, 5 Drawing Sheets

GLYCOPEPTIDE COMPOSITION WITH IMPROVED ANTIBIOTIC ACTIVITY

This application is a U.S. national stage application of International Application No. PCT/DK2004/000632, filed Sep. 17, 2004, which claims priority to EP03021000.9, filed Sep. 17, 2003, incorporated by reference herein in its entirety.

FIELD OF THE INVENTION

The present invention relates to a glycopeptide composition with improved antibiotic activity, use thereof as a pharmaceutical, and a method for producing a glycopeptide composition with improved antibiotic activity.

BACKGROUND OF THE INVENTION

Glycopeptide antibiotics can be classified in four groups based on their chemical structure:
- Group I (or the vancomycin type) has aliphatic amino acids at positions 1 and 3;
- Group II (or the avoparcin type) has aromatic amino acid residues at positions 1 and 3;
- Group III (or the ristocetin type) is similar to group II but for an ether linkage joining the aromatic amino acids at positions 1 and 3; and
- Group IV (or the Teicoplanin type) has the same amino acid arrangement as group III plus a fatty acid residue attached to the amino sugar.

(Yao, R. C. and Crandall, L. W., Glycopeptides, Classification, Occurrence, and Discovery in Glycopeptide antibiotics, ed. Nagarajan, R., Marcel Dekker, Inc., N.Y, N.Y., Chapter 1, pp. 1-27 (1994)).

Teicoplanin is a glycopeptide antibiotic produced by *Actinoplanes teicomyceticus* and was discovered during a scientific research program aiming to find new molecules of microbial origin that inhibited bacterial cell wall synthesis. (Goldstein, B. et al, Teicoplanin in Glycopeptide Antibiotics, ed. Nagarajan, R., Marcel Dekker, Inc., N.Y, N.Y., Chapter 8, pp. 273-307 (1994)). It was first described in 1978 and ten years later it was introduced into clinical practice in Italy. (Parenti, F. et al, J. Chemotherapy, Vol. 12, pp. 5-14, (2000)).

Teicoplanin shares many chemical and microbiological characteristics with vancomycin, but it possesses higher activity against many Gram-positive bacteria and is less nephrotoxic. (Parenti, supra; Janknegt, R., (1991), Teicoplanin in Perspective, Pharmaceutisch Weekblad Scientific Edition, 13: 153-160).

The molecular structure of Teicoplanin is depicted in FIG. 1. Like all glycopeptide antibiotics, Teicoplanin contains a core linear heptapeptide, in which five of the seven amino acids are common to all the members of its group. The remaining two (positions 1 and 3) are linked together by an ether bond. (Yao, supra). Three sugar moieties are attached to the aryl groups of amino acids 7, 6 and 4, namely a D-mannose, an N-acetyl-D-glucosamine and an N-acyl-D-glucosamine, respectively. These sugars have no biological activity in vitro, but have been found to impart different pharmacokinetic properties. (Reynolds P. E., Eur. J. Clin. Microbiol. Infect. Dis., Vol. 8, No. 11, pp. 943-950, (1989)).

Teicoplanin comprises different components, including five closely related molecules denoted Teicoplanin A2-1 (TA2-1) to Teicoplanin A2-5 (TA2-5), which differ only in the nature of the acyl moiety ($C_{10}$ and $C_{11}$ fatty acids); RS-1 to RS-4; a more polar component Teicoplanin A3-1 (TA3-1), which lacks the N-acyl-D-glucosamine residue and Teicoplanin TA3-2, which also lacks the D-mannose group. Substitution of the sugar residues with hydrogens results in the core aglycone, which is considered as a Teicoplanin A3 component. The molecular structures of the different components are shown in FIG. 2 herein.

U.S. Pat. No. 4,239,751 to Coronelli et al. describe isolation of different Teicoplanin components. Also illustrated in Table IV therein is that TA3 has a lower antibiotic activity than TA2.

U.S. Pat. No. 4,994,555 to Panzone et al. describes recovery of Teicoplanin from aqueous solutions from fermentation broths. Panzone et al. further describes "[a]s employed in its biological application Teicoplanin essentially consists of factor A2 (T-A2) accompanied by minor amount of factor A3 (T-A3)". (Column 2, lines 51-53).

Coronelli et al.: "Teicoplanin: Chemical, Physico-chemical and Biological Aspects", in Farmaco, Edizione Scientifica (1987), 42 (10), 767-86, state that a typical teicoplanin production batch contains no more than 12% TA3-1 and about 10% water.

Malabarba et al.: "Teicoplanin, Antibiotics from Actinoplanes Teichomyceticus nov. sp, Journal of Antibiotics 1984 Japan, vol. 37, no. 9, 1984, 988-999, states that they, starting from teicoplanin, prepared a crude material (intermediate composition) which contained 74% TA3-1 and 16% TA3-2 (HPLC).

SUMMARY OF THE INVENTION

In a first aspect, there is provided a glycopeptide antibiotic composition, such as a pharmaceutical composition, comprising
A: a glycopeptide antibiotic in its glycosylated form; and
B: a moiety of a glycopeptide antibiotic which lacks one or more glycosyl units; the content of B being about 16% to about 73% (w/w) of the total content of glycopeptides and deglycosylated glycopeptides in A resp. B, i.e. calculated as: B/(A+B) (w/w).

A can be selected from the group consisting of: Glycopeptide group I (vancomycin type); Glycopeptide group II (avoparcin type); Glycopeptide group III (ristocetin type); and Glycopeptide group IV (teicoplanin type); derivatives of any of these; and combinations thereof; and B is a deglycosylated moiety (such as a moiety lacking the easiest hydrolysable glycosylic group) of a glycopeptide selected from the group consisting of: Glycopeptide group I (vancomycin type); Glycopeptide group II (avoparcin type); Glycopeptide group III (ristocetin type); Glycopeptide group IV (teicoplanin type); derivatives of any of these; and combinations thereof. Especially interesting are glycopeptides of groups I and IV. Presently, the most interesting glycopeptides are teicoplanin and vancomycin.

In one embodiment, the invention relates to a glycopeptide antibiotic composition which comprises B in the range of about 18% to about 70%, but the range can also be selected amongst the ranges of: about 20% to about 60%, about 21% to about 55%, about 22% to about 55%, about 25% to about 50%, and about 21% to about 70%.

The present invention provides also a Teicoplanin composition comprising Teicoplanin components or a salt thereof, wherein the composition comprises % (mg TA3)/(mg TA3+mg TA2) of about 16% to about 73% as measured by HPLC analysis. In a further embodiment, there is provided a Teicoplanin composition which comprises Teicoplanin components or a salt thereof, wherein the composition comprises % (mg TA3)/(mg TA3+mg TA2) of about 21% to about 60% as measured by HPLC analysis. Other interesting ranges are 17% to 70%, 18% to 65%, 19% to 75%, 20% to 75%, 22% to 60%, 23% to 55%, 21% to 70%, 25% to 60%, 25% to 50%, all values are understood as "about".

In yet another aspect, the invention provides a Teicoplanin composition comprising TA2 and TA3, obtainable by a method selected from the group consisting of:
 a) a method comprising hydrolyzing a composition comprising TA2;
 b) a method comprising hydrolyzing a composition comprising TA2 by treating the composition containing TA2 with an acid or an enzyme;
 c) a method comprising hydrolyzing a composition comprising TA2, wherein the hydrolysis is performed on a crude Teicoplanin composition obtained from fermentation, without separation of the Teicoplanin components TA2 and TA3; and
 d) a method comprising hydrolyzing a composition comprising TA2 by treating the composition containing TA2 with an acid or an enzyme, wherein the hydrolysis is performed on a crude Teicoplanin composition obtained from fermentation, without separation of the Teicoplanin components TA2 and TA3;
which Teicoplanin composition is characterized by:
 a) a ratio TA3/(TA2+TA3) (w/w) that is not higher than 73%; and
 b) a ratio TA3/(TA2+TA3) (w/w) that is not lower than 16%. In an interesting embodiment, the weight of TA3 is calculated as the weight of TA3-1 and weight of TA2 is calculated as the total weight of the components TA2-1, TA2-2, TA2-3, TA2-4 and TA2-5, and in another embodiment, a) is not higher than about 70%; and b) is not lower than about 18%.

The present invention provides, in a further embodiment, a vancomycin composition comprising:
A: a vancomycin antibiotic, or a derivative thereof, in its glycosylated form; and
B: a vancomycin antibiotic, or a derivative thereof, which lacks one or two glycosyl units on the peptide skeleton, such as vancomycin aglycon or vancomycin which lacks the vancosamine;
the content of B being about 10% to about 90% (w/w) of the total content of vancomycin and deglycosylated vancomycin, i.e. calculated as: B/(A+B) (w/w). In other embodiments, the content of B is selected from the ranges: from about 13% to about 80% (w/w); from about 15% to about 70%; from about 20% to about 60%, and from about 25% to about 55%.

In yet another embodiment the invention relates to a pharmaceutical composition comprises a pharmaceutically acceptable amount of the glycopeptide composition, Teicoplanin composition or vancomycin composition of the invention; and a pharmaceutically acceptable carrier.

In another embodiment, the invention relates to a method of treating a microorganism infection in a patient comprises administering the glycopeptide composition, Teicoplanin composition or vancomycin composition of the invention to a patient.

In still another embodiment, a method for making a Teicoplanin composition with improved antibiotic activity comprises
 (i) making two or more Teicoplanin compositions comprising different % (mg TA3)/(mg TA3+TA2) of about 5% to about 60% as measured by HPLC analysis;
 (ii) analyzing the antibiotic activity of the compositions;
 (iii) identifying a composition where there is a synergistic effect of TA2 and TA3 and which has a desired improved antibiotic activity.

In one embodiment, a method for producing a Teicoplanin composition comprising TA2 and TA3, comprises hydrolyzing a composition containing TA2.

DETAILED DESCRIPTION OF THE INVENTION

It has been unexpectedly discovered that a positive synergistic effect of increased antibiotic activity of a Teicoplanin composition can be obtained by using a proper ratio of the amounts of TA2 and TA3 in the composition. It is known in the art that relatively pure TA3 has lower antibiotic activity than TA2. Contrary to the teaching in the art, it was found that within a certain window of % (mg TA3)/(mg TA3+TA2), it was possible to make a Teicoplanin composition with improved antibiotic activity due to a synergistic effect of TA2 and TA3 in the composition. By adding increasing amounts of TA3 to get an increased TA3:TA2 ratio, the antibiotic activity can greatly be improved. Not wishing to be bound by theory, it is contemplated that this synergistic effect is common the group of glycopeptide antibiotics that share a common mode of action, i.e. inhibit a late stage in bacterial cell wall peptidoglycan synthesis (cf. Reynolds in Eur. J. Clin. Microbiol. Infect. Dis. November 1989, p. 943-950).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term TA2 is a standard short name for Teicoplanin A2. Herein, this term comprises Teicoplanin having three carbohydrate moieties, such as the five closely related molecules denoted Teicoplanin A2-1 (TA2-1) to Teicoplanin A2-5

Figure 1:
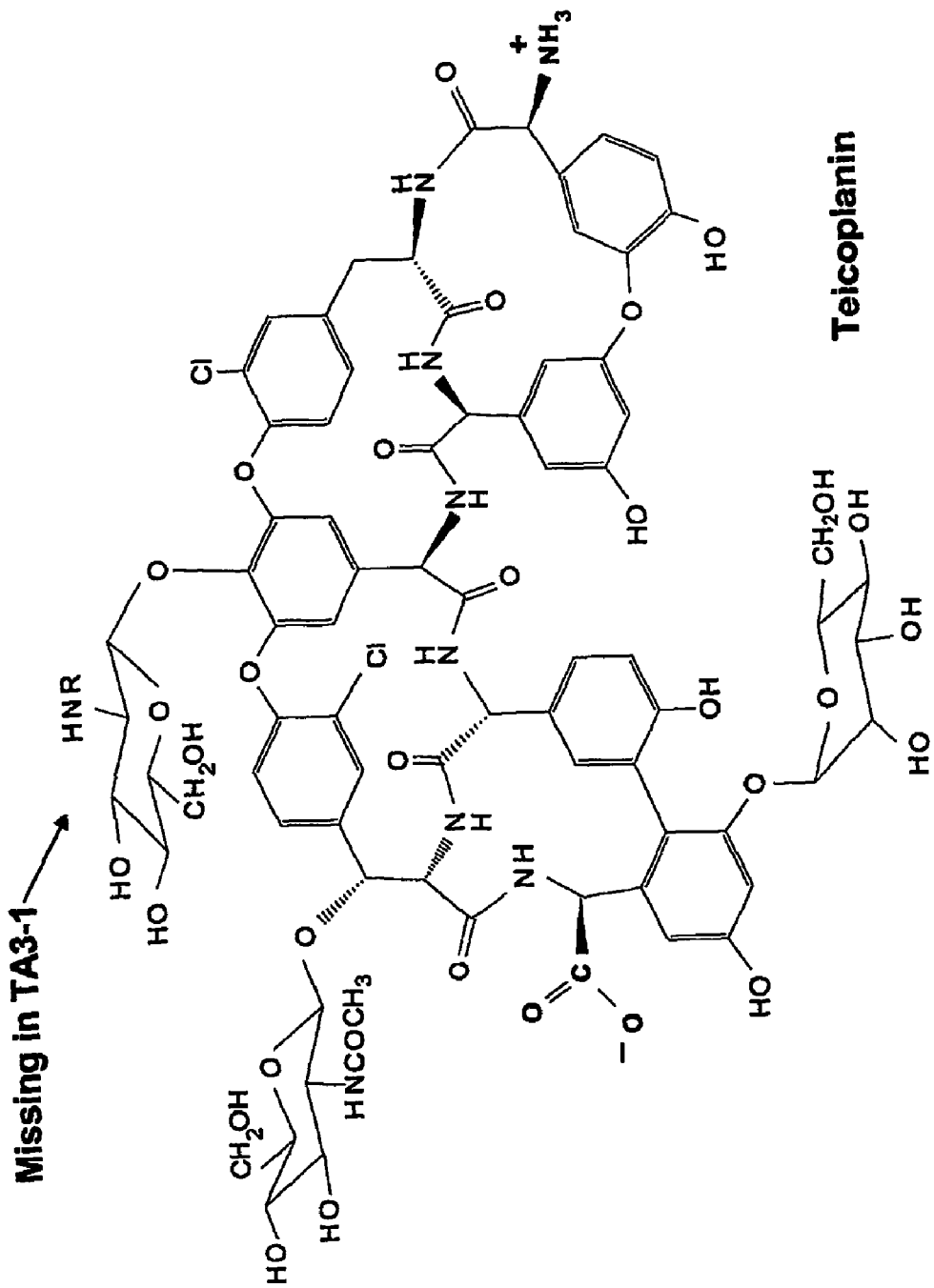
FIG. 1 illustrates the molecular structure of the Teicoplanin complex.
Figure 2:
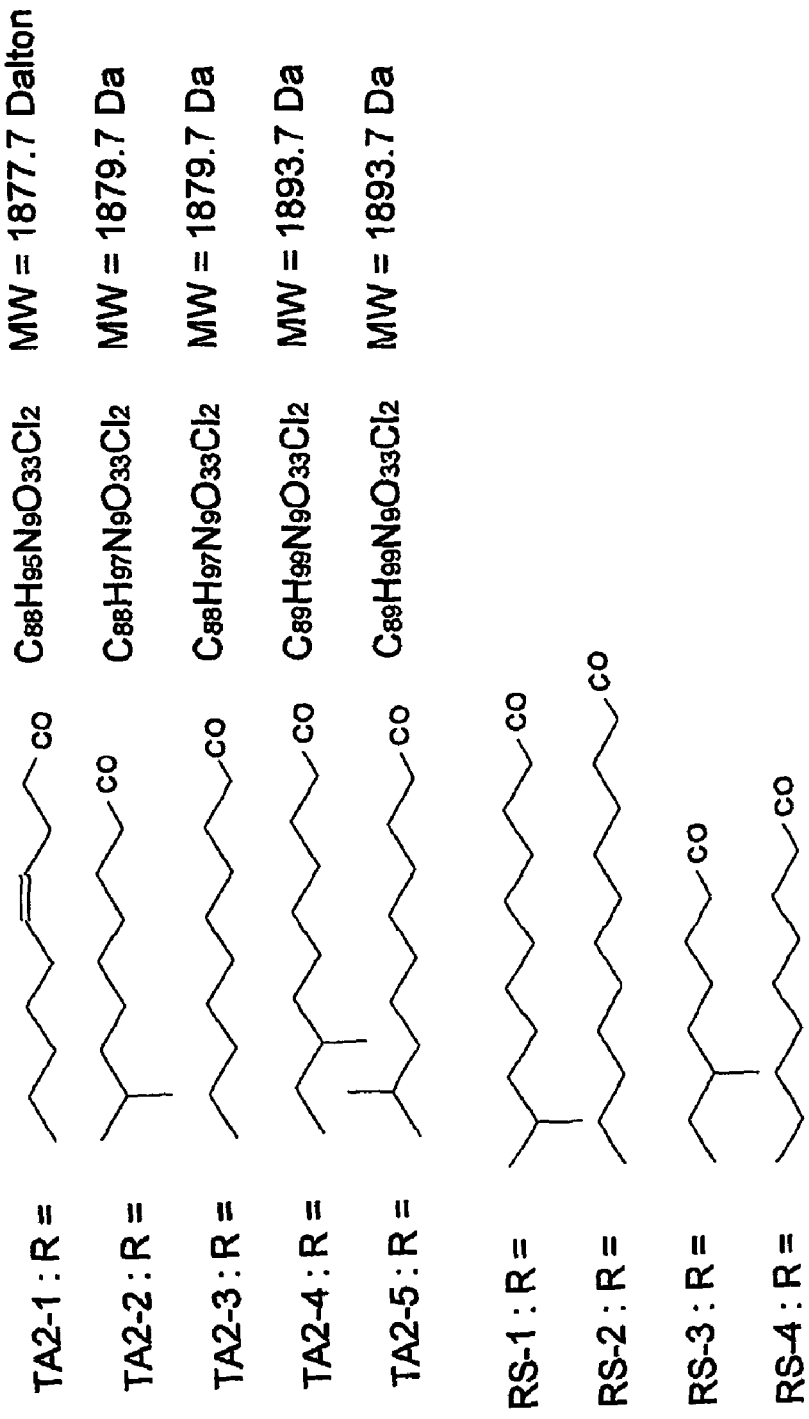
FIG. 2 illustrates the molecular structure of the different Teicoplanin components.

(TA2-5) and RS-1 to RS-4. Also, the term TA2 comprises derivatives thereof, such as derivatives that have been altered in the substituent R (see FIG. 1). Examples on R are given in the prior art and are known to the skilled person. Examples on molecular structures of different TA2 components are shown in FIGS. 1 and 2 herein. Specifically, the term TA2 denotes herein the Teicoplanin components selected from the group consisting of Teicoplanin A2-1 (TA2-1) to Teicoplanin A2-5 (TA2-5) and RS-1 to RS-4, or the term denotes the sum of two or more Teicoplanin components with three carbohydrate moieties, such as the sum of the 2, 3, 4, 5, 6, 7 or more of the most predominant Teicoplanins (with three carbohydrate moieties) in the composition. More preferably the term TA2 denotes herein the Teicoplanin components selected from the group consisting of Teicoplanin A2-1 (TA2-1) to Teicoplanin A2-5 (TA2-5), such as only the Teicoplanin component TA2-2, or the sum of these, i.e. the Teicoplanin A2 group (A2-1+A2-2+A2-3+A2-4+A2-5). More specifically, TA2 represents the sum: A2-1+A2-2+A2-3+A2-4+A2-5.

The term TA3 is a standard short name for Teicoplanin A3. Herein, this term comprises Teicoplanin components having two (e.g. TA3-1), one (e.g. TA3-2) or no carbohydrate moieties (e.g. Teicoplanin aglycone), either individually or in combination (e.g. the amount of all Teicoplanins having two or less carbohydrate moieties or the sum of TA3-1 and TA3-2). Specifically, the term TA3 denotes herein only the Teicoplanin component TA3-1. The molecular structures of TA3-1 and TA3-2 are shown in FIGS. 1 and 2 herein.

The specific amounts of TA3 and TA2 (or other glycopeptides, derivatives thereof and deglycosylated moieties of these) in a composition can be determined by any suitable means; for example by known analytical techniques such as High Performance Liquid Chromatography (HPLC) analysis. Briefly, such an HPLC analysis comprises the following steps: (i) having a suitable sample solution of a specified amount of the composition, (ii) performing the HPLC test with a suitable amount of the sample solution according to suitable standard operating conditions, and measuring the peak area of TA2 and the peak area of TA3 by a suitable automatic integration method. A suitable HPLC-analysis protocol is provided in Example 1 herein.

As used herein, "glycopeptide composition", such as "Teicoplanin composition" is inclusive of any salt forms, solvates (including hydrates), and derivatives. Derivatives include esters and/or ethers of any or all of the free hydroxy or phenol groups of the Teicoplanin component. Other derivatives may include alkylated, acylated, or acetylated amino group of the sugar moiety. Detailed description of such salt forms, derivatives, etc, are provided herein.

Figure 3:
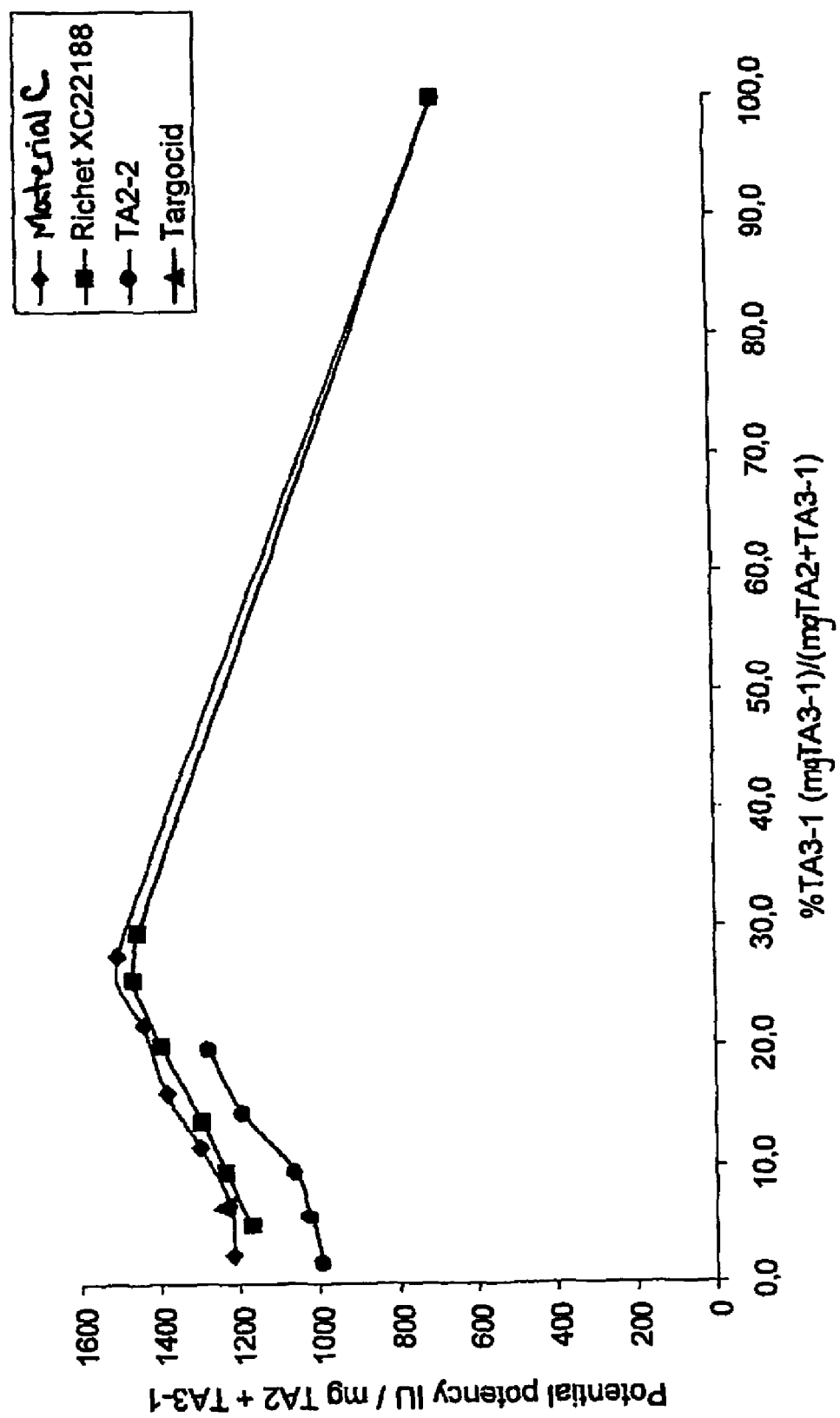
FIG. 3 is a graphical presentation of data that shows that by mixing in TA3-1 it was possible to make a Teicoplanin composition with higher antibiotic activity than TARGOCID.
Figure 4:
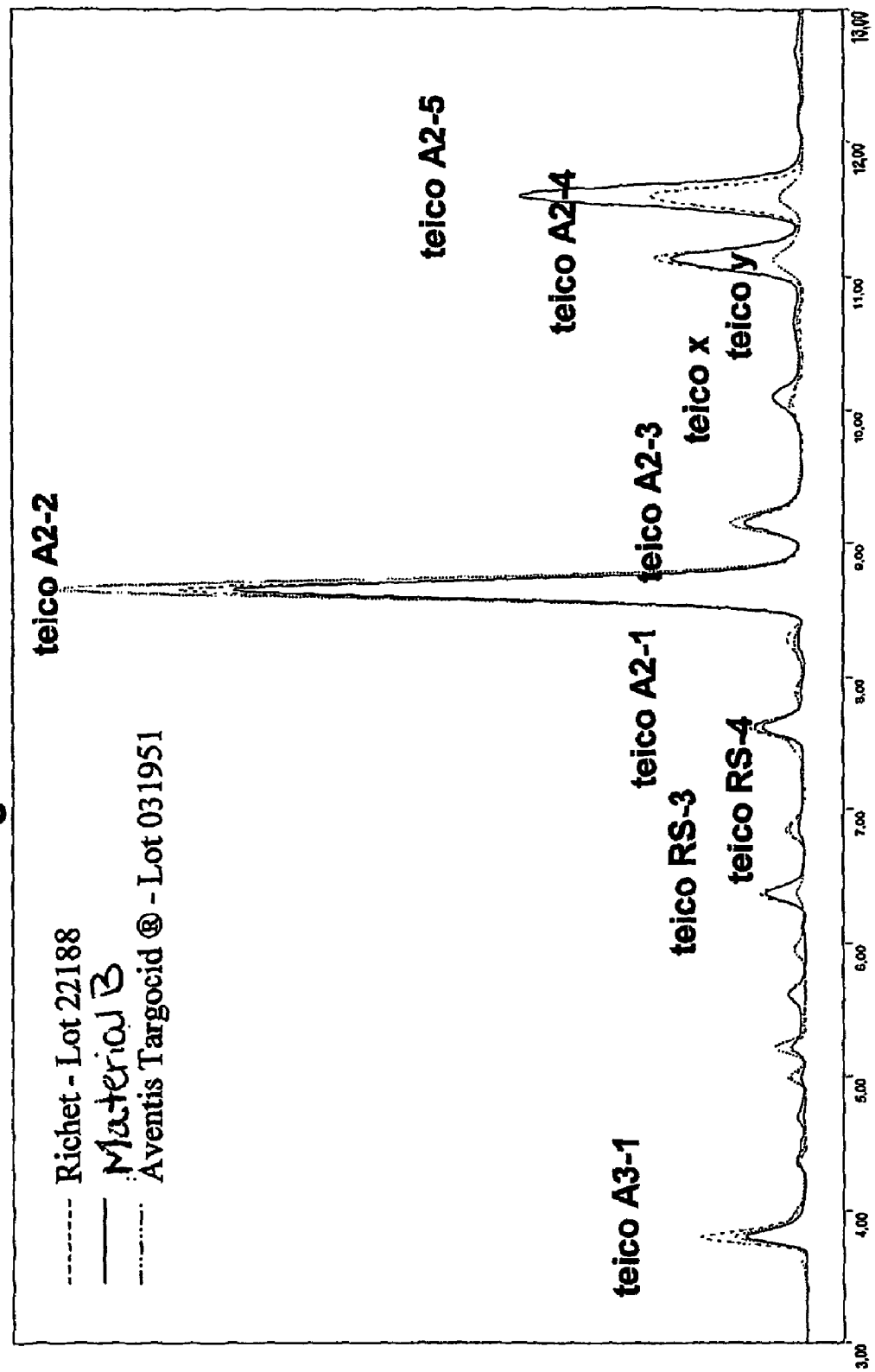
FIG. 4 shows an HPLC diagram of three Teicoplanin compositions.

As mentioned, it was found that within a certain window of % (mg TA3)/(mg TA3+TA2), it was possible to make a Teicoplanin composition with improved antibiotic activity due to a positive synergistic effect of TA2 and TA3 in the composition. FIG. 3 illustrates an example of the improvement in antibiotic activity of a Teicoplanin composition. The commercial Teicoplanin product TARGOCID was used as a reference composition. Based on a standard in the art known HPLC analysis of TARGOCID it was determined that TARGOCID has a % (mg TA3-1)/(mg TA3-1+TA2) of around 6.5%. (TARGOCID is a commercial Teicoplanin product from Aventis Pharma, and the determined ratio of 6.5% complies with the Official Japanese Monograph for Teicoplanin (JP Ministry of Health), which states that a teicoplanin composition must comprise not less than 80.0% A2 components (A2-1 to A2-5), not more than 15.0% A3 components (A3-1), and "other" not more than 5.0%, calculated as disclosed in the monograph). The data of FIG. 3 shows that by the addition of TA3-1 to various compositions it was possible to make a Teicoplanin composition with higher antibiotic activity than TARGOCID. As shown, the graphs include a point for the commercially available TARGOCID. The graphs further include graphs of two Teicoplanin materials wherein the amount of TA3-1 was added in varying amounts to show the synergistic effect. The TA2-2 graph illustrates the addition of TA3-1 to purified TA2-2. Again a positive synergistic effect result. More specifically, within the range of % (mg TA3)/(mg TA3+TA2) from about 6.75% to about 60% the tested compositions had a clearly higher antibiotic activity than TARGOCID.

The Teicoplanin composition may comprise about 18 weight percent to about 40 weight percent TA3 based on the total of weight of TA3 and TA2 as measured by HPLC analysis. In one embodiment, the Teicoplanin composition comprises % (milligram (mg) TA3)/(mg TA3+TA2) in the range from about 20% to about 40%, measured by HPLC analysis, more specifically the Teicoplanin composition comprises % (mg TA3)/(mg TA3+TA2) in the range from about 23% to about 40%, measured by HPLC analysis, even more specifically the Teicoplanin composition comprises % (mg TA3)/(mg TA3+TA2) in the range from about 24% to about 40% and yet more specifically the Teicoplanin composition comprises % (mg TA3)/(mg TA3+TA2) in the range from about 25% to about 40%. Other examples of ranges applicable for the ratio of the deglycosylated glycopeptide in the compositions as defined herein have a value selected from about 11%, about 12%, about 13%, about 14%, about 15%, about 16%, about 17%, about 18%, about 19%, about 20%, about 21%, about 22%, about 23%, about 24%, about 25%, about 26%, about 27%; about 28%; about 29%; about 30%; about 31%; about 32%; about 33%; about 34%; about 35%; about 45%; about 50%; about 55%, about 60%, about 65%, about 70%, or about 80%, all values described herein can be combined freely to form ranges.

The Teicoplanin composition can comprise more than about 600 mg dry matter of active TA2 and TA3 components per gram (g) of dry matter of the composition, specifically more than about 700 mg dry matter of active TA2 and TA3 components, and more specifically more than about 800 mg dry matter of active TA2 and TA3 components.

Preparation of the Teicoplanin composition can be made in a relatively large amount in order to provide the Teicoplanin composition as a so-called bulk product. Such a bulk product can be used to make several individual pharmaceutical Teicoplanin compositions. Accordingly, the Teicoplanin composition can have a total weight of the composition of at least about 100 g, more specifically of at least about 500 g. The individual pharmaceutical composition can have a content of about 1 mg to about 1000 mg of Teicoplanin.

As explained above, the commercial Teicoplanin pharmaceutical composition TARGOCID has been used as a reference in experimental examples described herein. Based on the TA2 and TA3 identified synergistic effects, the present inventors were routinely able to prepare compositions with a better antibiotic activity than TARGOCID, which was determined to have a % (mg TA3-1)/(mg TA3-1+TA2) of 6.5% as measured by HPLC-analysis.

Accordingly, in one embodiment a Teicoplanin composition as described herein, has a higher antibiotic activity than a corresponding Teicoplanin composition that has a % (mg TA3)/(mg TA3+TA2) of 6.5%, where the antibiotic activity is measured by a microbiological agar diffusion assay using *Staphylococcus aureus* ATCC 6538 as test strain and the measured potential potency (IU per mg TA2+TA3/g composition) is used to calculate the antibiotic activity.

The logic behind the potential potency (IU per mg TA2+TA3) unit may be illustrated by looling at Table 3 herein. Here it can be seen that the antibiotic potency is measured for the composition as such (IU/mg composition). Since the amounts of TA2 and TA3 of the composition also is known it is possible to calculate the potential potency (IU per mg TA2+TA3) as shown in Table 3.

The potential potency of the Teicoplanin composition, as described herein, can be at least about 5 IU higher than the corresponding Teicoplanin composition that has a % (mg TA3)/(mg TA3+TA2) of 6.5%, more specifically it is at least about 30 IU higher than the corresponding Teicoplanin composition that has a % (mg TA3)/(mg TA3+TA2) of 6.5%, even more specifically it is at least about 50 IU higher than the corresponding Teicoplanin composition that has a % (mg TA3)/(mg TA3+TA2) of 6.5%, yet more specifically it is at least about 100 IU higher than the corresponding Teicoplanin composition that has a % (mg TA3)/(mg TA3+TA2) of 6.5%, and still yet more specifically it is at least about 150 IU higher than the corresponding Teicoplanin composition that has a % (mg TA3)/(mg TA3+TA2) of 6.5%. Under some circumstances it may be difficult to get more than 1000 IU higher activity.

The term "corresponding Teicoplanin composition that has a % (mg TA3)/(mg TA3+TA2) of 6.5%," should be understood as a standard reference composition in the sense that, beside the specific TA3+TA2 amounts, it should comprise the same components, salt and etc. as the Teicoplanin composition which is evaluated in relation to its a better antibiotic activity.

Any and all of the glycopeptides, deglycosylated glycopeptides and derivatives of these, such as Teicoplanin components, may be converted into salts, such as pharmaceutically acceptable salts, and derivatives, such as esters and ethers, and other chemical equivalents, which, within a glycopeptide composition, such as a Teicoplanin composition, as described herein, are all covered by the present invention. The salts and derivatives can be prepared by standard procedures known to one skilled in the art. Salts like sodium and potassium salts, for example, may be prepared by treating the glycopeptides, deglycosylated glycopeptides and derivatives of these, such as Teicoplanin components, with suitable sodium or potassium bases.

The pharmaceutically acceptable salts include metal salts such as sodium salt, potassium salt, secium salt and the like; or alkaline earth metals such as calcium salt, magnesium salt and the like.

Esters and ethers may be prepared by the methods given in the literature, for example, in Advanced Organic Synthesis, 4$^{th}$ Edition, J. March, John Wiley & Sons, pp. 388-389, 395-396 (1992). Suitable esters and ethers include $C_1$-$C_{12}$ straight or branched chain alkyl, $C_3$-$C_{12}$ cycloalkyl, and/or $C_6$-$C_{36}$ aryl. "Aryl" as used herein means a compound having the ring structure characteristic of benzene, naphthalene, phenanthrene, anthracene, and the like, for example phenyl ($C_6$-$H_5$) or naphthyl ($C_{10}H_7$). The alkyl or aryl group may be unsubstituted or substituted with hydroxyl, $C_6$-$C_{36}$ aryl, $C_3$-$C_6$ cycloalkyl, $C_1$-$C_{12}$ alkyl, halogen (i.e., F, Cl, Br, I), $C_1$-$C_{12}$ alkoxy, $C_1$-$C_{12}$ alkylthio, $C_1$-$C_{12}$ perfluoroalkyl, $C_6$-$C_{36}$ perfluoroaryl, pyridyl, cyano, nitro, amino, $C_1$-$C_{12}$ alkylamino, $C_1$-$C_{12}$ aminoalkyl, acyl, amido, and/or carbamoyl.

The amino group of the sugar moiety can be alkylated, acylated, or acetylated, e.g. with acid chlorides by standard procedures known to one skilled in the art. Suitable alkyl and acyl groups comprise those groups described above for ester and ether.

Chemical equivalents may be stable complexes with metal ions, e.g. transition metals like $La^{3+}$, $Sm^{3+}$, $Eu^{3+}$, $Gd^{3+}$, which are typical for tetramic acid derivatives and may be prepared by the methods given in the literature (K. Tanaka et. al., Chem. Pharm. Bull., Vol. 27, 1901 (1979); K. Matsuo, Chem. Pharm. Bull., Vol. 28, 2494, (1980)).

The double bonds of the alkyl side chain (R) may be reduced by the methods given in the literature, for example in P. N. Rylander, "Hydrogenation Methods", Academic Press, New York Chpt. 2, (1985), or may be hydrohalogenated by methods described by H. O. House in "Modern Synthetic Reactions", W. A. Benjymin, Inc., New York, pp 446-452, (1972). Hydroxylated derivatives may be produced by reaction of the double bonds with reagents such as $OsO_4$ as described in the literature, e.g. Chem. Rev. Vol. 80, 187 (1980).

Derivatives may also be formed by conversion of the double bonds into epoxides by oxidation, e.g. with MCPBA, as described in Advanced Organic Synthesis, 4$^{th}$ Edition, J. March, John Wiley & Sons, p. 826 (1992).

The glycopeptide composition, such as the Teicoplanin composition, may be prepared as a pharmaceutical composition, optionally comprising a pharmaceutically acceptable carrier. By "pharmaceutically acceptable carrier" as used herein is meant one or more compatible solid or liquid filler diluents, or encapsulating substances. By "compatible" as used herein is meant that the components of the composition are capable of being commingled without interacting in a manner which would substantially decrease the pharmaceutical efficacy of the total composition under ordinary use situations.

Some examples of substances which can serve as pharmaceutical carriers include, for example, salts; sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; water; pyrogen-free water; isotonic saline; and phosphate buffer solution; skim milk powder; as well as other non-toxic compatible substances used in pharmaceutical formulations.

The pharmaceutical composition may also comprise wetting agents, fillers and lubricants such as sodium lauryl sulfate, as well as coloring agents, flavoring agents, lubricants, excipients, tabletting agents, stabilizers, anti-oxidants and preservatives, and the like.

The glycopeptide pharmaceutical composition, such as the Teicoplanin pharmaceutical composition, as described herein can be administered intramuscularly, intravenously, orally, or by other modes of administration.

A glycopeptide pharmaceutical composition, such as a Teicoplanin pharmaceutical composition, as described herein, with other pharmaceutically active substances (e.g. streptomycin) can be prepared by mixing the active compounds with one or more pharmacologically tolerated auxiliaries and/or excipients such as, for example, fillers, emulsifiers, lubricants, masking flavors, colorants, or buffer substances, and converting the mixture into a suitable pharmaceutical form such as, for example, tablets, coated tablets, capsules, granules, powders, emulsions, suspensions, or solutions suitable for parenteral administration.

Examples of auxiliaries and/or excipients which may be mentioned are tragacanth, lactose, talc, agar, polyglycols, ethanol, and water. Suitable and preferred for parenteral administration are suspensions or solutions in water. It is also possible to administer the active substances as such, without vehicles or diluents, in a suitable form, for example, in capsules.

The composition, such as the Teicoplanin composition can be in the form of a powder (such as a powder for injection upon reconstitution with a suitable liquid), in particular a powder comprising sodium chloride or glucose. Presently contemplated is a powder with about 0.5% to about 15% sodium chloride by weight. Any conventional injection liquid (such as a dextrose solution, a glucose solution, distilled and de-ionized water, and normal saline solution) may be used as a liquid for reconstituting the powdered preparation described herein.

The pharmaceutical composition, as described herein, can be provided together with suitable pharmaceutically relevant instructions. The instructions may explain pharmaceutically relevant information such as e.g. qualitative and quantitative of the composition, pharmaceutical form, therapeutic indications and method of administration (including recommend doses).

Glycopeptide compositions, such as Teicoplanin compositions, are useful for the treatment of a microorganism infection in a patient, such as an infection with Gram-positive bacteria, in particular staphylococcal bacteria including methicillin-resistant strains. Other Gram-positive bacterial infections that may be treated with the compositions described herein include those caused by streptococci, enterococci, and the like. The term "patient" relates to an animal, such as a mammal, including a human patient. In one embodiment, it is a human patient. A pharmaceutical composition, as described herein, can be administered to animals, such as mammals, including humans, as pharmaceuticals on their own, in mixtures with another active ingredient, and in the form of pharmaceutical compositions that permit parenteral administration.

A pharmaceutical composition can be administered orally, intramuscularly, intravenously, or by other modes of administration.

As is customary, the galenic formulation and the method of administration as well as the dosage range which are suitable in a specific case depend on the species to be treated and on the state of the respective condition or disease, and can be optimized using methods known in the art.

Accordingly, on average, the daily dose of a glycopeptide composition, such as a Teicoplanin pharmaceutical composition, in a patient may be from about 0.05 mg/kilogram (kg) weight to about 50 mg/kg weight, more preferably from about 1 mg/kg weight to about 20 mg/kg weight.

A method for making a Teicoplanin composition with improved antibiotic activity comprises:
  (i) making two or more Teicoplanin compositions comprising different % (mg TA3)/(mg TA3+TA2) in the range from about 5% to about 60%, measured by HPLC analysis;
  (ii) analyzing the antibiotic activity of the compositions;
  (iii) identifying a composition where there is a synergistic effect of TA2 and TA3 and which have a desired improved antibiotic activity.

The global idea behind this method relates to the herein-identified synergistic effect of TA2 and TA3.

In step (i) is made two or more Teicoplanin composition(s) comprising different % (mg TA3)/(mg TA3+TA2) in the range from about 7.5% to about 50%, more specifically in step (i) is made two or more Teicoplanin composition(s) comprising different % (mg TA3)/(mg TA3+TA2) in the range from about 15% to about 40%, even more specifically in step (i) is made two or more Teicoplanin composition(s) comprising different % (mg TA3)/(mg TA3+TA2) in the range from about 20% to about 40%, and yet more specifically in step (i) is made two or more Teicoplanin composition(s) comprising different % (mg TA3)/(mg TA3+TA2) in the range from about 21% to about 40%. In one embodiment, four or more of the different Teicoplanin compositions are made in step (i).

In another embodiment the identified composition of step (iii), has a higher antibiotic activity than a corresponding Teicoplanin composition that has a % (mg TA3)/(mg TA3+TA2) of 6.5%, wherein the antibiotic activity is measured by a microbiological agar diffusion assay using *Staphylococcus aureus* ATCC 6538 as test strain and the measured potential potency (IU per mg TA2+TA3/g composition) is used to calculate the antibiotic activity. The assay and potential potency can be made as described above.

The method for making a Teicoplanin composition can further comprises:
  (iv) making a Teicoplanin pharmaceutical composition, comprising an effective amount of Teicoplanin components or a pharmaceutically acceptable salt or derivative thereof and a pharmaceutically acceptable carrier, wherein the % (mg TA3)/(mg TA3+TA2) of the pharmaceutical composition is a % that corresponds to the % of the identified composition of step (iii).

The term "corresponds" in this step (iv) should be understood quite broadly in the sense that the specific % (mg TA3)/(mg TA3+TA2) of the pharmaceutical composition may vary some with respect to the identified composition of step (iii). The % of the identified composition may be the optimal % with respect to antibiotic activity. However, the skilled person may choose to slightly modify this in a specific Teicoplanin composition for different reasons such as, for example, production economy.

The Teicoplanin pharmaceutical composition of step (iv) above can be a Teicoplanin composition having the characteristic of a Teicoplanin composition of the first aspect and related embodiments of the present invention as described previously.

A separate aspect of the invention relates to a Teicoplanin composition as described herein that has been obtained by a method for making a Teicoplanin composition as described herein. It can be determined by one of ordinary skill in the art without undue experimentation different strategies for making Teicoplanin compositions comprising different % (mg TA3)/(mg TA3+TA2). One exemplary method is to purify TA3 from a commercial Teicoplanin composition and use this purified TA3 to enrich a Teicoplanin composition of interest to make a composition with increased amounts of TA3.

In another example, TA2 may be transformed by hydrolysis into TA3, where the N-acyl-D-glucosamine group with the fatty acid tail is removed from the glycopeptide base structure (see FIG. 1 herein). In an exemplary embodiment, the hydrolysis is performed with the crude Teicoplanin product obtained from a fermentation process. The hydrolysis can be acidic, basic or enzymatic, such as carried out by means of acid treatment (presently preferred under mild conditions) and enzymes. Another exemplary way to obtain a Teicoplanin composition as described herein would be to adjust the fermentation conditions in a way that will give higher TA3 amounts in the fermentation product.

Accordingly, a separate aspect of the invention relates to a method for producing a Teicoplanin composition comprising TA2 and TA3, which is enriched with TA3 (compared to starting material), the method comprising hydrolysis of a composition containing TA2, such as a composition comprising TA2 and TA3 (such as a composition (starting material) having a ratio TA3/(TA2+TA3) (w/w) of more than about 0.01; about 0.03; about 0.05; about 0.07; about 0.08; about 0.09; about 0.10; or even more than about 0.11 or about 0.12), e.g. by treatment with an acid or an enzyme. The end product can be targeted to have a ratio lower than about 80%. The hydrolysis can be performed on a crude Teicoplanin composition obtained from fermentation, without separation of the Teicoplanin components TA2 and/or TA3. The hydrolysis can be carried out under mild conditions, such as under conditions where pH is higher than 0, such as higher than about 1, or about 2, or even higher than about 3. When the hydrolysis is carried out as an acidic hydrolysis, it is presently contemplated that the hydrolysis is carried out at a pH value between 0 and about 5, or by using hydrochloric acid at a concentration between about 0.1 N and 1 N. The Teicoplanin can be dissolved in a polar organic solvent (such as an alcohol) or a mixture herewith with water during the hydrolysis. An optional step of the method for producing the Teicoplanin composition comprises mixing of a composition comprising TA3 and/or TA2 with the hydrolysis product, in order to obtain a standardized Teicoplanin composition. The added composition itself may be produced by hydrolysis or by fermentation. Advantageously, the hydrolysis of TA2 into TA3 should be partially complete (e.g. not full hydrolysis of all TA2), in order to directly obtain a Teicoplanin composition having a desired ratio TA3/(TA2+TA3).

In a further aspect, a Teicoplanin composition is obtainable by the methods described above. The obtainable composition can have a ratio TA3/(TA2+TA3) (w/w) of less than about 0.95 (such as less than about 0.9; about 0.8; about 0.7; about 0.6; about 0.5; about 0.4 or even less than about 0.35) and a ratio TA3/(TA2+TA3) (w/w) of more than 0.05 (such as more than 0.07; 0.08, 0.09; 0.10; 0.11; 0.12; 0.13; 0.14; 0.15; 0.16; 0.17; 0.18; 0.19; 0.20; 0.21; 0.22; 0.23 or even more than 0.25). The above ratios are also applicable for other compositions of the invention, calculated as B/(A+B) (w/w). In one embodiment, the ratio TA3/(TA2+TA3) (w/w) in the Teicoplanin composition is higher than 5% but lower than 90%; and the ratio TA3/(TA2+TA3) (w/w) is different from 6.5% (e.g. outside the range 6.25% to 6.75%, or outside the range 6% to 7%) as well as different from 10% (e.g. outside the range 9.75% to 10.25%, or outside the range 9.5% to 10.5%) as well as different from 15 to 20 percent (e.g. outside the range 14.75% to 20.25%, or outside the range 14.5% to 20.5%). TA3 can specifically be TA3-1 and/or TA2 can be the sum: (TA2-1+TA2-2+TA2-3+TA2-4+TA2-5).

Experimential:

EXAMPLE 1

Analyzing the Synergistic Effect of TA3-1 and TA2-2 in Different Compositions

Teicoplanin sources used in the following examples can be found in Table 1.

TABLE 1

| Source | Name | Lot |
|---|---|---|
| Aventis | Targocid | 031951 and 021972 |
| Alpharma | Material A | In house batches |
| | Material B | prepared from |
| | Material C | fermentation |
| Richet | Teicoplanina | 22188 |
| Xinchang Pharma (China) | Bulk Teicoplanin | 991022-6 |
| WHO*⁾ | International standard | WHO/NIBSC 90/704 |

*⁾For analysis a working standard is used, which has been calibrated against the WHO international standard.

Unless otherwise specified, all other materials described in the examples are standard laboratory chemicals. Unless otherwise specified, all equipment described in the examples is standard laboratory relevant equipment.

Purification of Teicoplanin A3-1.

To prepare a crude product with increased content of TA3-1 (Alpharma produced), Teicoplanin TA2 in 50% ethanol solution was converted by acid hydrolysis (1M HCl was added, resulting pH=0.6) at elevated temperatures to a crude mixture of TA2 and TA3 (including TA3-2 and the T-aglycone) and freeze dried.

To prepare pure TA3-1, the material from Xinchang Pharma was purified by preparative reversed phase C18 HPLC. The resulting solution was purified by normal phase HPLC to remove excess salt and dried to form a powder. The identity of the components was confirmed by flow injection analysis liquid chromatography mass spectrometry (FIA-LC-MS).

Purification of Teicoplanin A2-2.

Pure TA2-2 component was prepared by utilizing the same methods as for TA3-1.

Procedure for the HPLC Analysis for the Determination of Activity.

The HPLC method routinely used in the down stream process laboratory is as follows:

| | |
|---|---|
| Column: | Waters Xterra ® RP18, 3.5 µm, 4.6 × 150 mm |
| Precolumn: | Waters Xterra ® RP18 Guard column, 5 µm, 3.9 × 20 mm |
| Column oven: | 28° C. |
| Buffer: | 0.2% ammonium formate, pH 7.0 |
| | 4.0 g ammonium formate was dissolved in approximately 2 liters (l) of Milli-Q water. The pH was adjusted to 7.0 with $NH_3$. and the total volume was adjusted to accurately 2.0 l with Milli-Q water. The buffer was filtered through a 0.45 µm filter before use. |
| Mobile phase: | Eluent A: 90% buffer |
| | 10% acetonitrile (ACN) |
| | Eluent B: 35% buffer |
| | 65% ACN |

The mobile phase gradient for the HPLC analysis is presented in Table 2 with time in minutes (min) and flow in milliliters per minute (ml/min).

TABLE 2

| Step | Time (min) | Flow (ml/min) | % A v/v | % B v/v | Curve[1] |
|---|---|---|---|---|---|
| 0 | 0 | 1.5 | 85 | 15 | 6 |
| 1 | 1 | 1.3 | 73 | 27 | 6 |
| 2 | 3.5 | 1.3 | 72 | 28 | 11 |
| 3 | 13 | 1.5 | 60 | 40 | 6 |
| 6 | 13.5 | 1.5 | 0 | 100 | 6 |
| 7 | 15 | 1.5 | 0 | 100 | 6 |
| 8 | 16 | 1.5 | 85 | 15 | 6 |
| 9 | 23 | 1.5 | 85 | 15 | 6 |
| 10 | 30 | 0.05 | 85 | 15 | 6 |

[1]6 refers to a linear gradient and 11 refers to a delayed step gradient

The detection of the components was made using a UV detector at 280 nanometers (nm).
HPLC Standard: TARGOCID, 0.210 g/l.

Ten to 200 µl, corresponding to 2.1-42 µg Teicoplanin A2, was injected for a 5-point calibration curve, recorded in the beginning of the sequence and after every 30th sample. Variance in the response (=the total area of the five TA2 components) up to ±3% was accepted. Variance in retention time up to 10% was also accepted.

Preparation of Downstream Samples.

Liquid samples were diluted with 25 mM HEPES-buffer, pH 7, until approximately 0.25-2 g/l and 20 µl of the diluted sample were injected. Solutions used for potency determinations were prepared and 20 µl directly injected.

Powders were weighed, approximately 25 mg, into a 25 ml measuring flask and dissolved in 25 mM HEPES-buffer, pH 7 and 20 µl were injected.

Preparation of HEPES-buffer: 2.98 g HEPES was dissolved in approximately 450 ml of Milli-Q water. pH was adjusted to 7.0 with NaOH. The total volume was adjusted to accurately 500 ml with Milli-Q water.

The chromatograms were automatically integrated in range of 3 to 13 minutes by "valley to valley baseline" in the Waters Millenium software and the areas of the defined peaks TA3-1, TA2-1, TA2-2, TA2-3, TA2-4 and TA2-5 were recorded. All mass calculations (mg activity/g powder) were performed automatically by the software utilizing the calibration curve for TA2 and the sequence information about the weight of the samples and the dilutions. The combined area of the five TA2 components was used for calculations of the content of mg TA2/g powder. To calculate the content of TA3-1 the area of that peak was multiplied by a factor of 0.83 to compensate for the lower molecular weight of TA3-1. The percentage distribution of TA3-1 and TA2 was manually calculated by dividing the respective mass of TA3-1 and TA2 respectively by the total mass, i.e. mg(TA3-1)/mg(TA3-1+TA2).

Procedure for the Determination of Microbiological Potency by Agar Diffusion

Potency of Teicoplanin TA2, TA3-1 alone or in combination was determined by agar diffusion assays. Furthermore, the antimicrobial effect of pure and spiked products was investigated through the determination of the minimum inhibitory concentration (MIC) by a modified "MIC" test in micro titer trays.

The potency test is carried out according to the assay described below. The assay method generally corresponds to USP 25 and Ph.Eur 4th ed., but differs from both with respect to test strain and from the USP with respect to agar holes (ponds) as preferred to cylinders. The test is carried out as a 2,2 design as described in section <111> of the USP.

Materials and Specific Equipment:

| | |
|---|---|
| Media: | Antibiotic nutrient agar (Difco) art: 0001-01-8. |
| Buffer: | 0.2M phosphate buffer, pH 8.0 |
| Test organism: | *Staphylococcus aureus* ATCC 6538 or *Bacillus subtilis* ATCC 6633. |
| Antibiotic standard: | Working standard calibrated against the USP standard and Ph. Eur. standard. Alternatively USP or Ph. Eur. ref. standard. |
| Large plates: | Glass with aluminium frame (28.5 × 28.5 cm). |

Stock solutions of standards and samples were prepared to approximately 900 IU/ml. The Teicoplanin standard contained approximately 25.0 mg in 4.0 ml water and buffer ad 25.0 ml. The samples of Teicoplanin compositions contained approximately 25.0 mg in 4.0 ml water and buffer ad 25.0 ml. The amount of sample was adjusted according to the actual amount of standard weighed. Finally, the standard and sample were diluted with buffer to the following concentrations:

| 2-point assay: | |
|---|---|
| Solution 1 High: | approx. 400 IU/ml |
| Solution 2 Low: | approx. 100 IU/ml |

The standard or sample was applied to the plates in accordance with an 8×8 Latin square design. Immediately after application, place the plates in the incubator at 34.0° C.±2° C., for 16-18 hours.

The results are analyzed by reading the zone diameters carefully with a 10× magnification and a precision of 0.1 mm. Statistical evaluation: for calculation and validation, follow the guidelines set out in Ph. Eur. and USP, using a computer program for all calculations.

In the spiking experiments, the amount of the investigated sample (amount of powder weighed) was reduced and replaced by a corresponding amount of spiking material or stock solutions were mixed in defined ratios.

Determination of MIC Values and Results.

Pure TA3-1, (Teicoplanin Material B 96% TA2-X, 4% TA3-1) and mixtures thereof were used. The test strain used was *S. aureus* ATCC 6538 in final concentrations of $5 \times 10^5$/ml and $5 \times 10^4$/ml respectively. The test was carried out in micro titer trays as a modification of an ordinary MIC test. Instead of using two-fold dilutions, 0.40-1.20 µg/ml with 0.20 µl divisions and 1.0-4.0 µl/ml with 1.0 µl divisions was used. The trays were incubated at 37° C. The wells were examined after 24 hours and any visible growth was noted. The "MIC" value was defined as the lowest Teicoplanin concentration that did not show visible growth.

A series of spiking experiments with different levels of TA3-1 were performed and the potency of the resulting mixtures was determined by agar diffusion. The results are summarized in Table 3.

TABLE 3

| Sample | TA2 content mg/g powder | TA3 content mg/g powder | Potency IU/mg powder | Potential potency IU/mg (TA2 + TA3-1) |
|---|---|---|---|---|
| Targocid working standard | 690 | 48 | 917 | 1243 |
| TA3-1 | 1 | 829 | 570 | 687 |
| Richet | 612 | 32 | 811 | 1226 |
| Richet | 605 | 32 | 761 | 1195 |
| Richet + 5% TA3-1 | 627 | 67 | 856 | 1233 |
| Richet + 10% TA3-1 | 601 | 96 | 896 | 1286 |
| Richet + 15% TA3-1 | 562 | 142 | 987 | 1402 |
| Richet + 20% TA3-1 | 528 | 183 | 1054 | 1482 |
| Richet + 25% TA3-1 | 504 | 214 | 1068 | 1487 |
| Material A. NaCl | 585 | 27 | 745 | 1217 |
| Material A. NaCl + 11.8% TA3-1 | | | 890 | |
| Material A. NaCl + 13.5% TA3-1 | 581 | 156 | 980 | 1330 |
| Material A. NaCl + 20% TA3-1 | 555 | 222 | 1020 | 1312 |
| Material A. NaCl + 21.1% TA3-1 | | | 965 | |
| Material B | 731 | 27 | 828 | 1092 |
| Material B + 5% TA3-1 | 705 | 68 | 930 | 1204 |
| Material C | 788 | 19 | 982 | 1217 |
| Material C + 5% TA3-1 | 750 | 55 | 988 | 1227 |
| Material C + 10% TA3-1 | 721 | 96 | 1061 | 1299 |
| Material C + 15% TA3-1 | 680 | 132 | 1124 | 1384 |
| Material C + 20% TA3-1 | 632 | 177 | 1163 | 1438 |
| Material C + 25% TA3-1 | 584 | 224 | 1214 | 1502 |
| TA2-2 | 770 | 23 | 807 | 1017 |
| TA2-2 + 5% TA3-1 | 744 | 65 | 874 | 1080 |
| TA2-2 + 10% TA3-1 | 694 | 106 | 955 | 1194 |
| TA2-2 | 767 | 14 | 776 | 994 |
| TA2-2 + 5% TA3-1 | 785 | 49 | 853 | 1023 |
| TA2-2 + 10% TA3-1 | 753 | 81 | 886 | 1062 |
| TA2-2 + 15% TA3-1 | 709 | 121 | 990 | 1193 |
| TA2-2 + 20% TA3-1 | 666 | 166 | 1065 | 1280 |
| TA2-2 + 25% TA3-1 | | | 1093 | |

TA2 is the total content of TA2-1 to TA2-5, and
TA3 is the content of TA3-1.

All spiking experiments clearly revealed a synergistic effect of TA3-1 in the potency tests by agar diffusion. In order to strengthen the evidence some experiments were performed with a modified antimicrobial analysis of Teicoplanin, spiked with different amounts of TA3-1. It was carried out in liquid medium in contrast to the agar diffusion tests and determined the MIC values. The results are summarized in Table 4, ("MIC"-values of Teicoplanin and/or TA3-1 on *S. aureus* ATCC6538).

TABLE 4

| Sample | MIC (μg/ml) $5 \times 10^5$/ml S. aureus | MIC (μg/ml) $5 \times 10^4$/ml S. aureus |
|---|---|---|
| Material B (a) | 0.6 | 0.4-0.6 |
| TA3-1 (b) | 2-3 | 2-3 |
| 90% (a) + 10% (b) | 0.4-0.6 | 0.4 |

The results from this study indicate a much lower potency of TA3-1 (570 IU/mg powder) than that of TA2-2 (807 IU/mg). Just adding the effect of the content of A3-1 in high potency products would thus not by itself explain the higher potency. The only reasonable explanation would be that TA3 in combination with TA2 in the appropriate amounts adds a synergistic effect.

In this study different amounts of TA3 were added to a range of different Teicoplanin products, including the purified TA2-2 single component, with variable microbial potencies alone. Replacing from 5 to 25% of Teicoplanin sample with the corresponding amount of TA3-1 invariably increased the microbial potency of the sample, measured in IU/mg powder. The data also proved that the potential (=the actual quality of the Teicoplanin in the powder) increased when active TA2 was replaced by low active TA3-1, indicating a synergistic effect between TA2 and TA3. The results can be visualized in a graphic plot as shown in FIG. 3 herein. FIG. 3 contains the data from the standard, the Richet compositions, material C compositions, and the TA2 compositions.

Comparing the potential potencies (IU/mg TA2+TA3-1) in FIG. 3, a synergistic effect of TA3-1 with the other Teicoplanin components is visible in the plot. Even products with high potency are improved when some of the TA2 is replaced with TA3-1. As also can be seen from FIG. 3 the synergistic effect seems to occur when the ratio of TA3-1 to total TA2+TA3-1 is above 5% and to increase steadily as the amount of TA3-1 increased.

The results from the MIC determination supported the findings by agar diffusion assays. The antimicrobial effect of TA3-1 alone on *S. aureus* was much lower than that of Teicoplanin.

EXAMPLE 2

Analysing the Synergistic Effect of TA3-1 and TA2 in Different Compositions

Materials:
The following teicoplanin sources are used.

| Source | Name | Lot |
|---|---|---|
| Aventis | Targocid, content (defined as mg active compound/mg powder): 85% | 031951 |
| Alpharma | TA3-1: content: 80% | TKO.004-06-24 |

*) For analysis a working standard is used, which has been calibrated against the WHO international standard.

All other materials described in the examples are standard laboratory chemicals.

Methods

Experiment Setup

Three experiments were performed on solutions of Targocid and TA3-1 alone or mixed at different ratios aiming at the following TA3%:

Series 1: 0; 20; 25; 30; 35 and 60%
Series 2: 10; 15; 20; 25; 40 and 80%
Series 3: 15; 30; 35; 40; 50 and 100%

HPLC Determination of Activity

The HPLC-analysis for determination of activity is equal to the method described in example 1. The content mg/g powder of the five TA2 components (=TA2) and TA3-1 respectively were analyzed, and TA3-1% was calculated as (mTA3-1)/mTA2+mTA3-1), where "m" is defined as mg active compound/mg powder.

Bioassays

Potency of teicoplanin TA2, TA3-1 alone or in combinations was determined by agar diffusion assays as described in example 1. Modified MIC-values in microtitre trays were determined as described in example 1.

Results

Figure 5:
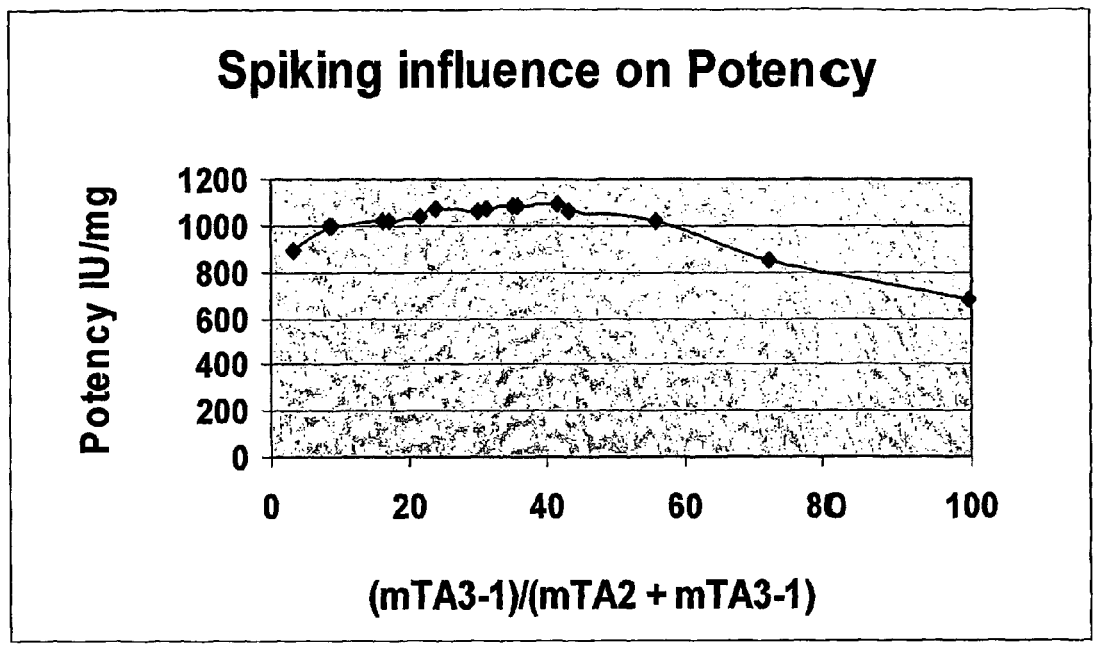
FIG. 5 is a graphical presentation of data that shows the influence of spiking teicoplanin A2 with teicoplanin A3-1 on the potency of the composition.

FIG. 5 shows a graph summary of the potency results IU/mg powder against the mass TA3-1% from all the spiking experiments. This graph shows an increased potency by agar diffusion until up to 40% TA3-1, after whichthe potency decreased. When the TA3-1% was above 70% the potency had decreased to the level as Targocid alone or below.

Figure 6:
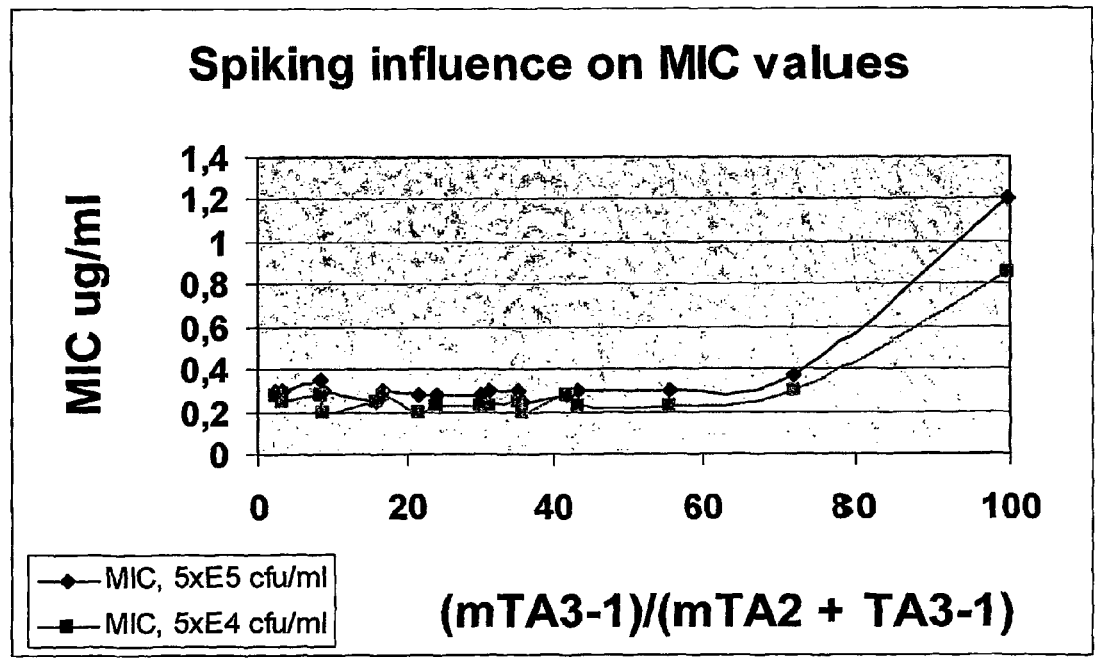
FIG. 6 is a graphical presentation data that shows the influence of spiking teicoplanin A2 with teicoplanin A3-1 on the MIC of the composition.

FIG. 6 shows a graph summary of the MIC values μg powder/ml solution against the mass TA3-1% from all the spiking experiments. The MIC values keep the same levels until approximately 60% of Targocid has been replaced by TA3-1. At higher TA3-1% the MIC-values start to increase to end with a MIC value of pure TA3-1, which is 4-5 times higher than for Targocid alone.

The results from this study indicate a much lower potency of TA3-1 alone than that of Targocid. Replacing up to about 40% of TA2 with the corresponding amount of TA3-1 invariably increased the microbial potency of the sample, measured in IU/mg powder, and not until about 70% TA3-1 the potency was found less than for Targocid alone. Just adding the effect of the content of A3-1 would thus not by itself explain the higher potency. The only reasonable explanation would be that TA3-1 adds a synergistic effect.

The results from the MIC determination supported the findings by agar diffusion assays. The antimicrobial effect of TA3-1 alone on *S. aureus* was 4-5 lower than that of teicoplanin TA2. Still up to about 60% of Targocid could be replaced with TA3-1 without any increase in MIC values. Even though a decrease in MIC values could not be found at increasing amounts of TA3-1, the unexpectedly stable MIC-values up to 60% can only be explained by a synergistic effect between TA2 and TA3-1.

Through this study evidence for the proposed synergy effect between Teicoplanin A2 and A3 is provided. The mechanism of this synergy is yet unclear, but both agar diffusion and MIC determinations of pure and spiked samples have shown there is a true synergistic effect between TA3 and TA2.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical vancomycin antibiotic composition comprising
   A: a vancomycin antibiotic in its glycosylated form; and
   B: aglucovancomycin;
   the content of B being 11% to 60% (w/w) of the total content of glycopeptides and deglycosylated glycopeptides, calculated as: B/(A+B) (w/w),
   and a pharmaceutically acceptable carrier or excipient.

2. A pharmaceutical composition comprising a pharmaceutically acceptable amount of the composition according to claim 1; and a pharmaceutically acceptable carrier.

3. The composition of claim 1, wherein the content of B is 20% to 60%.

4. The composition of claim 1, wherein the content of B is 25% to 55%.

5. The composition of claim 1, wherein the content of B is 11% to 55%.

6. A unit dosage form for pharmaceutical use, comprising a vancomycin antibiotic composition which comprises:
   A: a vancomycin antibiotic in its glycosylated form; and
   B: aglucovancomycin;
   the content of B being 11% to 60% (w/w) of the total content of glycopeptides and deglycosylated glycopeptides, calculated as: B/(A+B) (w/w),
   and a pharmaceutically acceptable carrier or excipient.

* * * * *